United States Patent
Dugan et al.

(10) Patent No.: US 10,010,064 B2
(45) Date of Patent: Jul. 3, 2018

(54) METHODS AND COMPOSITIONS FOR TREATING A HOOF OF AN UNGULATE ANIMAL

(71) Applicant: Kerr Corporation, Orange, CA (US)

(72) Inventors: Frank Dugan, Belton, MO (US); Frank Rovelli, Ventura, CA (US); Paul Wittrock, Newbury Park, CA (US)

(73) Assignee: Kerr Corporation, Orange, CA (US)

( * ) Notice: Subject to any disclaimer, the term of this patent is extended or adjusted under 35 U.S.C. 154(b) by 6 days.

(21) Appl. No.: 14/046,366

(22) Filed: Oct. 4, 2013

(65) Prior Publication Data

US 2015/0096503 A1    Apr. 9, 2015

(51) Int. Cl.
*A01L 15/00* (2006.01)
*A01L 5/00* (2006.01)
(Continued)

(52) U.S. Cl.
CPC .......... *A01L 15/00* (2013.01); *A01L 5/00* (2013.01); *A61K 9/0017* (2013.01); *A61K 47/34* (2013.01);
(Continued)

(58) Field of Classification Search
CPC ..... A01L 1/00; A01L 1/02; A01L 3/00; A01L 3/02; A01L 5/00; A01L 15/00
(Continued)

(56) References Cited

U.S. PATENT DOCUMENTS 3,118,449 A    1/1964  Bane
3,682,179 A    8/1972  Firth et al.
(Continued)

FOREIGN PATENT DOCUMENTS

JP    2003199469 A    7/2003
JP    2011246593 A    12/2011
(Continued)

OTHER PUBLICATIONS

JP 2011-246593 machine translation.*
(Continued)

*Primary Examiner* — Son T Nguyen
(74) *Attorney, Agent, or Firm* — Sheppard, Mullin, Richter & Hampton LLP

(57) ABSTRACT

A method of treating a hoof of an ungulate animal. The method comprises coating one or both of (i) at least a portion of a bottom surface of the hoof or (ii) at least a portion of a block surface with a curable polymer and allowing the polymer to cure for a period of time. The polymer is cured within 60 seconds or less of the coating and the cured polymer has a Shore D hardness of about 10 to about 50. The curable polymer is provided as a two component system. The first component is a reaction product of (a) comprises 4-4'-diphenylmethane-diisocyanate, castor oil, isocyanatopropyltriethoxysilane, and glycidoxypropyltrimethoxysilane, and wherein (b) comprises dicyclohexylmethane-4,4-diisocyanate, polyether polyol, 4,4'-diphenylmethane-diisocyanate (MDI), and triethoxy(3-isocyanatopropyle) silane. The second component comprises polyoxypropylene oxide ether polyol, diol (2000 MW), polyoxypropylene oxide ether polyol, triol (450 MW), tetrahydroxypropylethylendiamine, metaxylenediamine, and organobismuth catalyst.

12 Claims, 2 Drawing Sheets

(51) Int. Cl.
| | |
|---|---|
| C08G 18/76 | (2006.01) |
| C08G 18/71 | (2006.01) |
| C08G 18/38 | (2006.01) |
| C08G 18/75 | (2006.01) |
| C08G 18/32 | (2006.01) |
| C08G 18/22 | (2006.01) |
| A61K 9/00 | (2006.01) |
| A61K 47/34 | (2017.01) |
| C08G 18/72 | (2006.01) |
| C08G 18/36 | (2006.01) |
| C08G 18/48 | (2006.01) |
| C08G 18/66 | (2006.01) |
| C08G 18/00 | (2006.01) |
| C09J 175/04 | (2006.01) |

(52) U.S. Cl.
CPC ......... *C08G 18/003* (2013.01); *C08G 18/227* (2013.01); *C08G 18/324* (2013.01); *C08G 18/3206* (2013.01); *C08G 18/3284* (2013.01); *C08G 18/36* (2013.01); *C08G 18/3819* (2013.01); *C08G 18/3893* (2013.01); *C08G 18/4812* (2013.01); *C08G 18/6696* (2013.01); *C08G 18/718* (2013.01); *C08G 18/724* (2013.01); *C08G 18/758* (2013.01); *C08G 18/7671* (2013.01); *C09J 175/04* (2013.01)

(58) Field of Classification Search
USPC .............................. 168/4, 12, 13, 14, 26, 28
See application file for complete search history.

(56) References Cited

U.S. PATENT DOCUMENTS

| | | | | |
|---|---|---|---|---|
| 4,182,340 | A | | 1/1980 | Spencer |
| 4,869,400 | A | | 9/1989 | Jacobs |
| 4,888,225 | A | * | 12/1989 | Sandvig ............... A43D 999/00 168/12 |
| 5,069,289 | A | | 12/1991 | Schaffer |
| 5,681,350 | A | | 10/1997 | Stovall |
| 5,990,257 | A | * | 11/1999 | Johnston ............... C08G 18/10 528/28 |
| 6,001,946 | A | * | 12/1999 | Waldman ............... C08G 18/10 524/869 |
| 6,009,952 | A | | 1/2000 | Porteous et al. |
| 6,021,851 | A | | 2/2000 | Jacobs |
| 6,131,665 | A | | 10/2000 | Rovelli et al. |
| 6,196,326 | B1 | | 3/2001 | Jacobs |
| 6,197,912 | B1 | * | 3/2001 | Huang ................... C08G 18/10 525/453 |
| 6,231,972 | B1 | | 5/2001 | Fryer |
| 6,364,025 | B1 | | 4/2002 | Jacobs |
| 6,412,566 | B1 | | 7/2002 | Rovelli et al. |
| 6,497,292 | B2 | | 12/2002 | Rovelli |
| 6,505,686 | B2 | * | 1/2003 | Rovelli ................... A01L 11/00 168/4 |
| 6,528,595 | B1 | * | 3/2003 | Ikawa .................... C08G 75/12 257/E23.119 |
| 6,761,223 | B1 | * | 7/2004 | Rovelli ................... A01L 5/00 168/4 |
| 7,124,832 | B2 | | 10/2006 | Kelly |
| 7,319,128 | B2 | * | 1/2008 | Ziche ..................... C08G 18/22 525/403 |
| 7,834,123 | B2 | | 11/2010 | Suen |
| 8,505,162 | B2 | | 8/2013 | Pigg et al. |
| 9,200,160 | B2 | * | 12/2015 | Ramakrishnan ........ C08L 75/04 |
| 2003/0106699 | A1 | | 6/2003 | Reiss et al. |
| 2005/0121205 | A1 | | 6/2005 | Kelly |
| 2006/0173121 | A1 | * | 8/2006 | Tamai ................... C08G 65/336 524/502 |
| 2009/0124751 | A1 | * | 5/2009 | Lucas .................... C08G 18/10 524/507 |
| 2010/0288515 | A1 | | 11/2010 | Rovelli |
| 2010/0317796 | A1 | * | 12/2010 | Huang ................... C08G 18/10 524/588 |
| 2011/0237734 | A1 | * | 9/2011 | Ramakrishnan ........ C08L 75/04 524/500 |
| 2012/0244095 | A1 | | 9/2012 | Konradi et al. |
| 2013/0078473 | A1 | | 3/2013 | Kollbach et al. |
| 2013/0144006 | A1 | | 6/2013 | Derksen et al. |
| 2013/0197098 | A1 | * | 8/2013 | Geret ..................... A01N 25/04 514/724 |
| 2013/0245194 | A1 | * | 9/2013 | Huang ................... C08G 18/10 524/588 |
| 2015/0031806 | A1 | * | 1/2015 | Lim ....................... C08L 75/04 524/114 |

FOREIGN PATENT DOCUMENTS

| | | |
|---|---|---|
| JP | 2012097200 A | 5/2012 |
| WO | WO2010062318 A1 | 6/2010 |

OTHER PUBLICATIONS

Adhere 50 cc Kit, http://www.vettec.com/adhere-50cc-kit, 2003.
Instructions for Adhere 50cc, http://www.vettec.com/instructions-adhere-50cc, 2003.
Adhere 180cc—Black, http://www.vettec.com/adhere-180cc-black, 2003.
Adhere 180cc—Beige, http://www.vettec.com/adhere-180cc-beige, 2003.
Instructions for Adhere 180cc, http://www.vettec.com/adhere-180cc-instructions, 2003.
Equi-Build 180cc, http://www.vettec.comiequi-build-180cc, 2003.
Instructions for Equi-Build 180cc, http://www.vettec.com/equi-build-180cc-instructions, 2003.
Equi-Pak 180cc, http://www.vettec.com/equi-pak-180cc, 2003.
Instructions for Equi-Pak 180cc, http://www.vetteccom/equi-pak-180cc-instructions, 2003.
Equi-PaklCS 180cc, http://www.vettec.com/equi-pakcs-180cc, 2003.
Instructions for Equi-PaklCS 180cc, http://www.vettec.com/equi-pak-cs-180cc-instructions, 2003.
Equi-PaklSoft 180cc, http://www.vettec.com/equi-pak-soft-180cc, 2003.
Instructions for Equi-PaklSoft 180cc, http://www.vettec.com/equi-pak-soft-180cc-instructions, 2003.
Sil-Pak 180cc, http://www.vettec.com/sil-pak-180cc, 2006.
Instructions for Sil-Pak 180cc, http://www.vettec.cornisil-pak-180cc-instructions, 2006.
Sole-Guard 180cc, http://www.vettec.com/sole-guard-180cc, 2006.
Instructions for Sole-Guard 180cc, http://www.vettec.com/sole-guard-180cc-intructions, 2006.
Super Fast 50cc Kit, http://www.vettec.com/super-fast-50cc-kit, 2003.
Instructions for Super Fast 50cc, http://www.vettec.com/instructions-super-fast-50cc, 2003.
Super Fast 180cc, http://www.vettec.com/super-fast-180cc, 2003.
Instructions for Super Fast 180cc, http://www.vettec.com/super-fast-180cc-instructions, 2003.
International Search Report and Written Opinion of the International Searching Authority in application No. PCT/US2014/059137, dated Feb. 13, 2015.
European Search Report in application No. 14153524.5, dated Mar. 15, 2015.
Bovi Bond Block Adhesive Safety Data Sheet.
Equi-Build Safety Data Sheet.
Equi-Pak Safety Data Sheet.
Equi-Pak Soft Instant Pad Material Safety Data Sheet.
Equi-Thane 46145 Material Safety Data Sheet.
Equi-Thane Superfast, Adhere Beige and Adhere Black Safety Data Sheet.
Sole-Guard Safety Data Sheet.

* cited by examiner

METHODS AND COMPOSITIONS FOR TREATING A HOOF OF AN UNGULATE ANIMAL

FIELD OF THE INVENTION

The present invention relates generally to methods and compositions for treating a hoof of an ungulate animal.

BACKGROUND

Lameness remains a major cause of disease and economic loss in dairy, cow-calf, and feedlot operations. The impact of lameness on fertility, productivity, and farm economics has been well-documented. The majority of lameness in cattle involves the structures of the foot. Sole ulcers, white line disease (defects in the sole at the junction with the vertical hoof walls), and interdigital necrobacillosis (footrot) are the most common foot disorders that create lameness in cattle. If not treated promptly, these relatively superficial conditions can progress to create infection of bone, synovial structures, tendons, and ligaments of the digit. These deeper tissues may also become infected from puncture wounds, lacerations, injuries to the hoof, and progression of sole abscesses.

Deep infection of the foot is a challenging condition to treat. While commonly used, amputation of the digit may not be the best treatment option if the animal is heavy, maintained on range or a large dry-lot dairy, intended for natural breeding, or intended for long-term (>18-24 months) productivity. Medical and surgical treatments aimed at salvage of the affected digit may be more appropriate in such cases, although these cattle represent a therapeutic challenge to the veterinarian.

The treatment of cows present significant challenges in addition to their size and weight. Cows must be positioned on their sides in order to treat the diseased foot. Cows cannot, however, remain in this position for prolonged periods of time without risk of significant injury and possible death due to the significant weight imposed on its internal organs in the side-lying position. Thus, any treatment modality for cow feet must be performed and completed within a relatively quick period of time.

What is therefore needed is a method of treating or protecting a hoof of an ungulate animal, short of amputation or surgery, which may be performed in a relatively short period of time.

BRIEF SUMMARY

In one embodiment, a method of treating a hoof of an ungulate animal is provided. The method comprises coating one or both of (i) at least a portion of a bottom surface of the hoof or (ii) at least a portion of a block surface with a curable polymer and allowing the polymer to cure for a period of time. The polymer is cured within 60 seconds or less of the coating and the cured polymer has a Shore D hardness of about 10 to about 50.

In accordance with a first aspect, the coating is performed on the entirety of the bottom surface of the hoof.

In accordance with a second aspect, the cured polymer has a shore D hardness in the range of about 25 to about 35.

In accordance with a third aspect, the curable polymer is a polyurethane that is obtained by the reaction of a first and a second composition. The first composition is a mixture comprising unreacted isocyanate groups. The second composition comprises polyoxypropylene oxide ether polyol, diol (2000 MW), polyoxy propylene oxide ether polyol, triol (450 MW), tetrahydroxypropylethylenediamine, metaxylenediamine, and organobismuth catalyst.

In accordance with a fourth aspect, the first composition is a reaction product of (a) and (b), wherein (a) consists of: 4-4'-diphenylmethane-diisocyanate, castor oil, isocyanatopropyltriethoxysilane, and glycidoxypropyltrimethoxysilane, and wherein (b) consists of: dicyclohexylmethane-4,4-diisocyanate, polyether polyol, 4,4'-diphenylmethane-diisocyanate (MDI), and triethoxy(3-isocyanatopropyle)silane.

In accordance with a fifth aspect, the method further comprises co-extruding and mixing the first and second compositions before the coating.

In accordance with a sixth aspect, the polymer is cured within 30 seconds of the coating.

In accordance with a seventh aspect, the polymer is cured after 15 seconds of the coating.

In accordance with an eighth aspect, the method further comprises applying a block to the bottom surface of the hoof after the coating but before the curing, wherein the curing adheres the block to the hoof.

In accordance with a ninth aspect, the curable polymer is a self-supporting paste prior to allowing the polymer to cure for a period of time.

In another embodiment, a protected hoof of an ungulate animal is provided. The protected hoof comprises a hoof of an ungulate animal having a hoof wall and a bottom surface and a cured polymer (i) covering at least a portion of the bottom surface of the hoof or (ii) adhering a block to a bottom surface of the hoof, the cured polymer having a hardness that is less than a hardness of the hoof wall.

In accordance with a first aspect, the cured polymer has a Shore D hardness of about 10 to about 50.

In accordance with a second aspect, the cured polymer has a Shore D hardness of about 25 to about 35.

In accordance with a third aspect, the cured polymer covers the entire bottom surface of the hoof.

In accordance with a fourth aspect, the cured polymer covers the block surface and the block is positioned on and adhered to the bottom surface of the hoof.

In accordance with a fifth aspect, the ungulate animal is selected from the group consisting of: a horse and a cow.

In accordance with a sixth aspect, the cured polymer is a polyurethane that is obtained by the reaction of a first and second composition. The first composition is a mixture comprising unreacted isocyanate groups. The second composition comprising polyoxypropylene oxide ether polyol, diol (2000 MW), polyoxy propylene oxide ether polyol, triol (450 MW), tetrahydroxypropylethylenediamine, metaxylenediamine, and organobismuth catalyst.

In accordance with a seventh aspect, the first composition is a reaction product of (a) and (b), wherein (a) consists of: 4-4'-diphenylmethane-diisocyanate, castor oil, isocyanatopropyltriethoxysilane, and glycidoxypropyltrimethoxysilane, and wherein (b) consists of: dicyclohexylmethane-4,4-diisocyanate, polyether polyol, 4,4'-diphenylmethane-diisocyanate (MDI), and triethoxy(3-isocyanatopropyle)silane.

In a further embodiment, a method of manufacturing a reactive polyurethane system is provided. The method comprises providing first and second components which are dispensible from first and second cartridges, respectively. The first component is a reaction product of (a) and (b). Component (a) comprises 4-4'-diphenylmethane-diisocyanate, castor oil, isocyanatopropyltriethoxysilane, and glycidoxypropyltrimethoxysilane, and component (b) comprises dicyclohexylmethane-4,4-diisocyanate, polyether polyol, 4,4'-diphenylmethane-diisocyanate (MDI), and triethoxy(3-isocyanatopropyle) silane. The second component comprises polyoxypropylene oxide ether polyol, diol (2000 MW), polyxoypropylene oxide ether polyol, triol (450 MW), tetrahydroxypropylethylendiamine, metaxylenediamine, and organobismuth catalyst.

In accordance with a first aspect, the method further comprises providing a mixing tip that is configured to couple the first and second cartridges and mix the first and second components as they are dispensed from the first and second cartridges, respectively.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Illustrative embodiments of the present disclosure are described herein with reference to the accompanying drawings, in which.

Like numerals refer to like parts throughout the several views of the drawings.

DESCRIPTION OF THE PREFERRED EMBODIMENTS

Figure 1A:
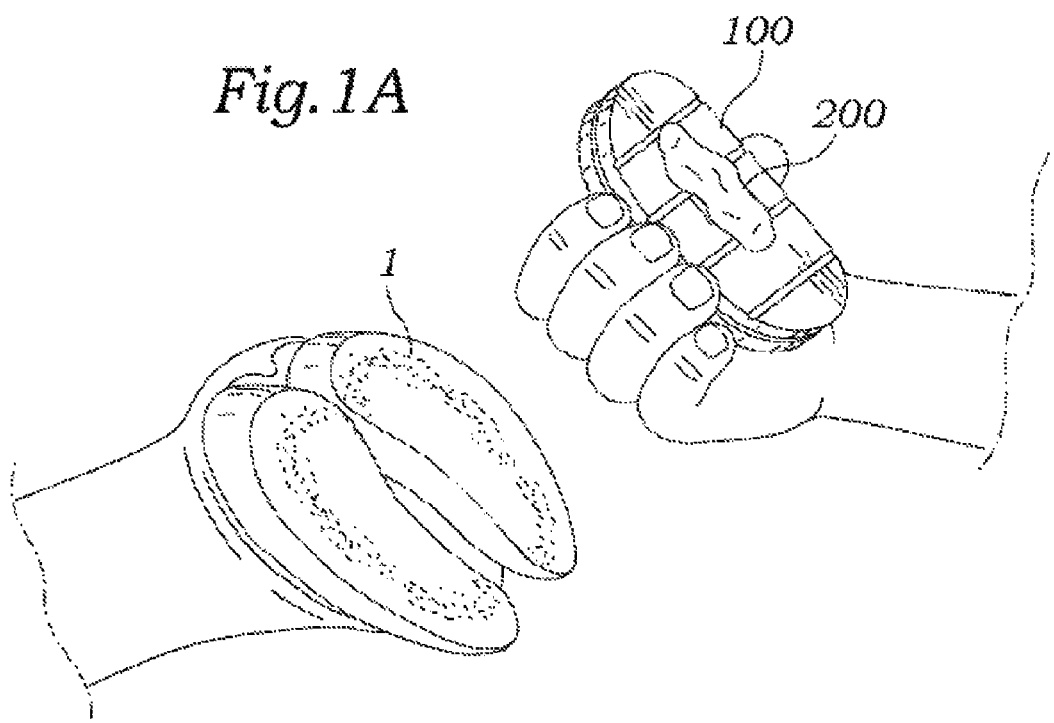
FIGS. 1A-1D depict the sequence of steps involved in treating a hoof of an ungulate animal using the compositions described herein.

Specific, non-limiting embodiments of the present invention will now be described with reference to the preferred embodiments. It should be understood that such embodiments are by way of example only and merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

Ungulate animals, such as cows, are typically maintained on dairy farms where movement is limited and the grounds are wet, soft and typically covered in manure. These conditions present unique challenges to the health of a cow's claw and to treating infections and rot of the claw. Once infected, the animal must avoid putting pressure on the infected portions and also avoid contact with the manure-covered grounds for healing to take place.

The methods and compositions described herein are directed to treating a hoof or claw of an ungulate animal. The methods and compositions include a curable polymer which is formed by reaction of at least two components. The curable polymer can be used to create a protective barrier on a surface, preferably a bottom surface, of the hoof or claw. Alternatively, the curable polymer can be used as a cushioned adhesive to couple a block or other protective device onto the hoof or claw.

The curable polymer has provides significant advantages based on its physical characteristics, cure time and sustained adhesive strength. Because the curable polymer is typically applied to a vertical surface, such as would be encountered when applying the polymer to a bottom surface of a hoof of a cow that is lying on its side, the curable polymer must be a self-supporting paste at the time it is applied to the hoof or block.

The curable polymer is produced by combining at least two reactive components or pre-polymers. While each one of the components may not have sufficient viscosity to itself be self-supporting, i.e., will not sag or run under the influence of gravity, once the components are combined, the resulting curable polymer will be self-supporting and will not run or sag significantly when applied onto a vertical surface.

At the same time, the curable polymer preferably has a relatively short curing time so as to avoid injury or death to the animal. In a preferred embodiment, the curing time is less than a minute, preferably less than 45 seconds and more preferably less than 30 seconds. The curing time, however, is preferably not be too short so as to preclude the ability to manipulate and spread the curable polymer across the surface of the hoof or block. In other words, the curable polymer retains sufficient viscosity for at least a minimum period of time as would be needed to apply, spread and extrude it to the outer sides of the wood block that is applied to the claw. Accordingly, the curing time is preferably at least 5 seconds, more preferably at least 10 seconds, and most preferably at least 15 seconds. In a preferred embodiment, the curing time is between 15 to 45 seconds. In other words, the curable polymer does not lose its viscosity for at least 5 seconds, preferably at least 10 seconds, and most preferably at least 15 seconds.

The material hardness of a polymer is typically associated with its adhesive strength, with harder polymers having greater adhesive strength and softer polymers being reduced adhesive strength. The curable polymers, once fully cured, is characterized as having relatively reduced material hardness as compared to the hardness of the hoof. In a preferred embodiment, the cured polymer has a shore D hardness of about 10 to about 50. In a particularly preferred embodiment, the shore D hardness is in the range of about 25 to about 35. One significant advantage to the reduced hardness is the cushioning provided by the cured polymer as the animal walks on hard surfaces or places its weight on the adhered block.

The cured polymer, while having a reduced material hardness, surprisingly has an adhesive strength that is substantially greater than would be expected based on its reduced material hardness. By virtue of its sustained adhesive strength, the cured polymer remains adhered to the hoof for at least an acceptable period of time for the cow to be rehabilitated, typically 15-30 days.

The methods and compositions described herein provide material advantages in connection with treating a hoof of an ungulate animal short of amputation or surgical treatment. FIGS. 1A-1D depict the sequence of steps involved in a treatment method in which a block is applied to one of the two claws, such that the other one of the two claws remains elevated from the ground. In a preferred embodiment, the block is applied to the healthy one of the claws while the infected claw remains elevated from the ground and thus relieved of pressure while standing and walking.

Figure 1B:
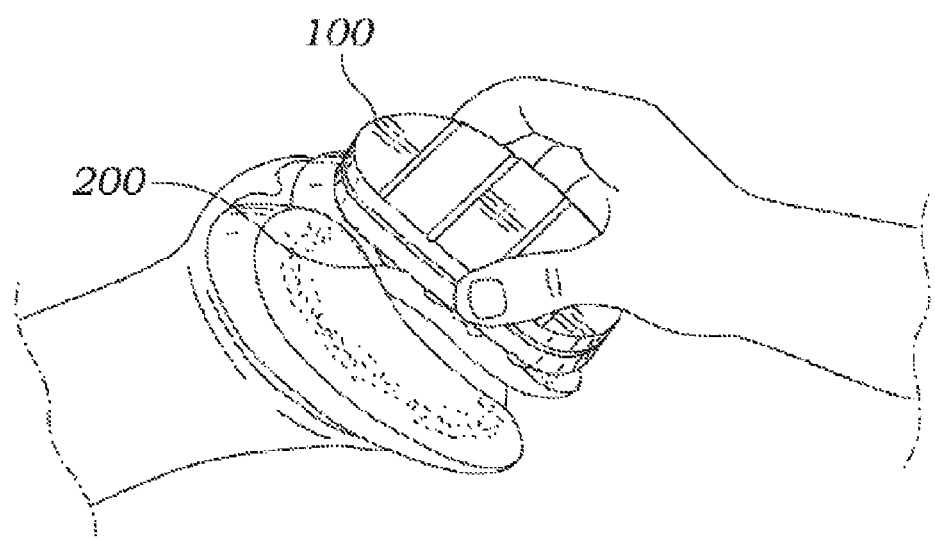
Figure 1C:
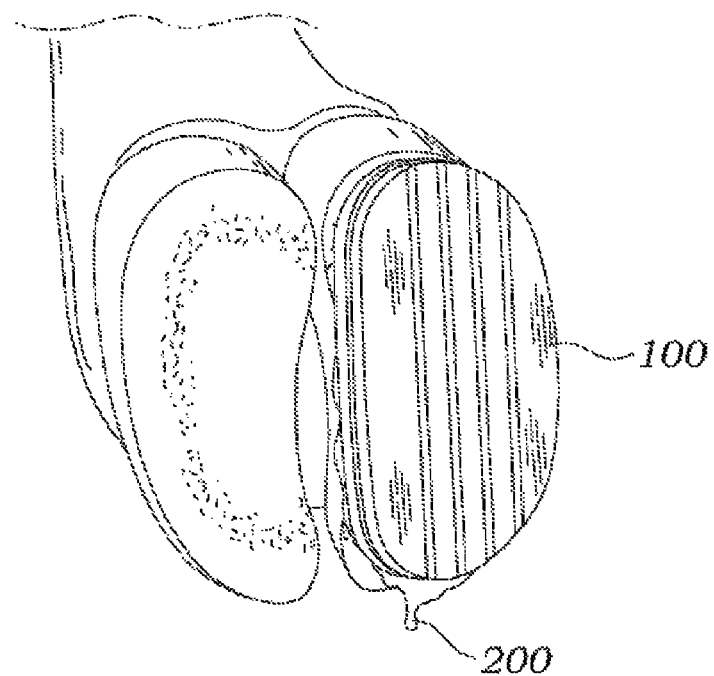
Figure 1D:
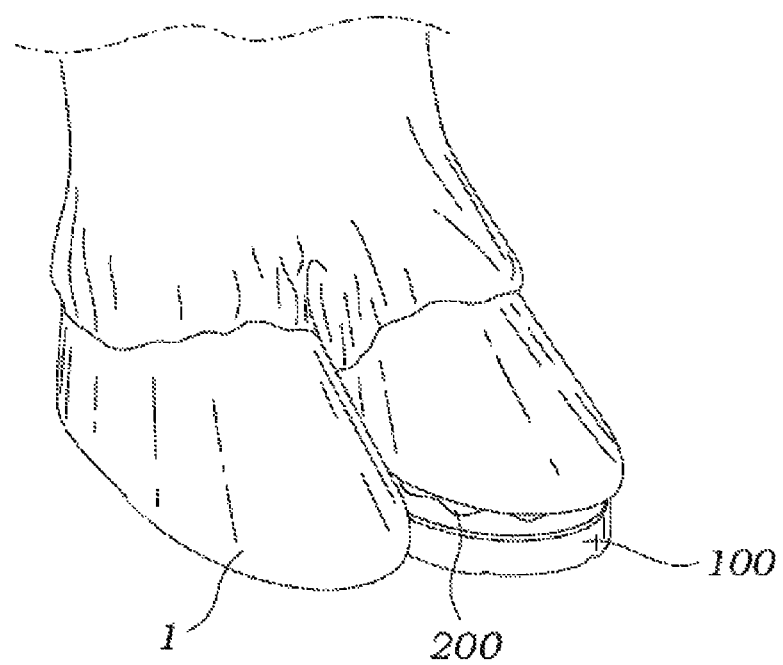

FIG. 1A depicts the preparation of a wood block 100 in which a polymer-adhesive composition 200 is applied to the surface of the wood block. The cow claw 1 is also depicted and as being leveled and balanced by trimming or rasping and sufficiently dried. FIGS. 1B-1C depicts the application of the wood block 100 to the healthy one of the two claws 1, with the polymer-adhesive 200 in between the claw 1 and the wood block 100. As can be seen, the polymer-adhesive 200 spaces the wood block 100 from the claw 1 and thus provides cushioning for the claw when the cow puts weight on the claw 1 when standing or walking. In a preferred embodiment, the polymer-adhesive 200 provides a 2-3 mm layer of cushioning. FIG. 1D depicts how the wood block 100 elevates the claw 1 from the ground after the polymer-adhesive 200 is completely set and cured and therefore weight-bearing.

In one embodiment, a polymer-adhesive composition is provided for use in the process of FIGS. 1A-1D. The polymer-adhesive composition has the advantageous features of being soft but yet highly adhesive. These two features are typically mutually exclusive in that the softer the polymer, the less adhesive it is. Similarly, the more adhesive the polymer, the greater the hardness. It is desirable to have a relatively soft polymer-adhesive because it will serve to cushion the claw against the block and thus be more comfortable for the animal to stand and walk on the adhered block. The adhesiveness will ensure that the block stays positioned on the claw for at least a period of time required for the infected claw to heal.

In another embodiment, the polymer-adhesive composition is applied onto at least a portion of the bottom surface of the claw or hoof, and preferably onto the entire bottom surface of the claw or hoof. In accordance with this embodiment, a block is not required and the polymer-adhesive layer is allowed to set and cure completely before permitting contact with a ground surface. The cured polymer-adhesive layer itself functions as a protective layer in instances where protection is desired for thin or sensitive hooves or where increased traction is desired as when the animals are walking on concrete or metal surfaces.

Example

The polymer-adhesive composition is a result of a three-component reactive polyurethane system which requires parallel formation of the reactive isocyanate portions. The reactive isocyanate portions are then combined and a resulting two-component system is provided. The concept of parallel isocyanate prepol formulation is contrary to standard serial formulation practice. Although this may add complexity to the manufacturing process, it results in a polymer-adhesive composition that is soft, adhesive and has a very short cure time. The constituents of each of the three components A1, A2 and B are provided below:

Composition A1

| Ingredient | Quantity |
| --- | --- |
| 4,4'-dipheylmethane-diisocyanate | 76.5% |
| Castor oil | 20.6% |
| Isocyanatopropyltriethoxysilane | 1.0% |
| Glycidoxypropyltrimethoxysilane | 1.9% |

Composition A2

| Ingredient | Quantity |
| --- | --- |
| Dicyclohexylmethane-4,4-diisocyanate | 20% |
| Polyether polyol | 55.24% |
| 4,4'-diphenylmethane-diisocyanate (MDI) | 15.24% |
| Triethoxy (3-isocyanatopropyl) silane | 9.52% |

Composition B

| Ingredient | Quantity |
| --- | --- |
| Polyoxy propylene oxide ether polyol, diol (2000 MW) | 53.5% |
| Polyoxy propylene oxide ether polyol, triol (450 MW) | 25.8% |
| Tetrahydroxypropylethylenediamine | 17.9% |
| Metaxylenediamine | 2.6% |
| Organobismuth catalyst | 0.2% |

The polymer-adhesive is produced by first combining compositions A1 and A2 to produce prepolymer A1-A2. The prepolymer A1-A2 is packaged separately from composition B and provided to the end-use uncombined and in separate containers. In a preferred embodiment, prepolymer A1-A2 and composition B are separately provided in first and second cartridges, respectively, and subsequently loaded onto a dispensing gun. Prepolymer A1-A2 and composition B may be combined by simultaneous extrusion via a mixing tip. Suitable dispensing guns are described in U.S. Pat. No. 6,505,686, issued Jan. 14, 2003 to Vettec, Inc., the entire contents of which are incorporated herein by reference in its entirety.

Once prepolymer A1-A2 and composition B is permitted to mix and react, the resulting polymer-adhesive will set within about 30 seconds and fully cure within 2-3 minutes. The cured polymer-adhesive is preferably characterized as having a Shore D hardness of about 10 to about 50 and preferably a Shore D hardness in the range of about 25 to about 35. The cushioning provided by the cured polymer-adhesive is optimal, particularly since it is softer than bovine hoof.

TABLE 1

Comparison of Hardness for Various Polymer-Adhesives

| Product | Hardness (Qualitative) | Hardness (Quantitative) |
| --- | --- | --- |
| Example | Optimum | 25-35 Shore D |
| Bovine Hoof | — | 50-60 Shore D |
| BoviBond ® | Hard | 60-80 Shore D |
| Equipak ® Soft | Soft | 10-20 Shore A |

TABLE 2

Comparison of the Characteristics of the Example and BoviBond ®

| Test: | Condition: | Example | BoviBond ® |
| --- | --- | --- | --- |
| Appearance: | Cured | Opaque, Flexible | Black, Rigid |
| Work Time: | 25° C. | 20-25 seconds | 20-40 seconds |
| Tack-Free Time: | 25° C. | 30-40 seconds | ≤50 seconds |
| Hardness | Cured, 1 hour @ 25° C. | 25-30 Shore D | 65-70 Shore D |
| | Cured, 24 hour @ 25° C. | 30-35 Shore D | 70-80 Shore D |
| Sag: | 25° C. | Non-Sag | Non-Sag |

The invention described and claimed herein is not to be limited in scope by the specific preferred embodiments disclosed herein, as these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

What is claimed is:

1. A method of creating an adhesive, protective barrier adapted to coat and adhere to a bottom surface of a hoof or a claw of an ungulate animal, the method comprising:
   combining first and second components to produce a self-supporting curable polymer,
   wherein the first component is a reaction product of (a) a composition comprising 4-4'-diphenylmethane-diisocyanate (MDI), castor oil, isocyanatopropyltriethoxysilane, and glycidoxypropyltrimethoxysilane, and (b) a composition comprising dicyclohexylmethane-4,4-diisocyanate, polyether polyol, 4,4'-diphenylmethane-diisocyanate (MDI), and triethoxy (3-isocyanatopropyle) silane;
   wherein the second component comprises polyoxypropylene oxide ether polyol, diol (2000 MW), polyoxypropylene oxide ether polyol, triol (450 MW), tetrahydroxypropylethylendiamine, metaxylenediamine, and organobismuth catalyst;
   wherein the curable polymer is self-supporting when applied onto a vertical surface; and
   allowing the polymer to cure for a period of time applying the polymer to a hoof or a claw of an ungulate animal.

2. The method of claim 1, wherein the cured polymer has a shore D hardness in the range of about 10 to about 50.

3. The method of claim 1, wherein the cured polymer has a shore D hardness in the range of about 25 to about 35.

4. The method of claim 1, further comprising co-extruding and mixing the first and second compositions through a mixing tip.

5. The method of claim 1, wherein the polymer is cured within 30 seconds after the combining.

6. The method of claim 1, wherein the polymer is cured within 15 seconds after the combining.

7. The method of claim 1, further comprising applying a block to the polymer after the combining, wherein the curing adheres the block.

8. The method of claim 1, wherein in the composition comprising the 4-4'-diphenyl methane-isocyanate (MDI), the castor oil, the isocyanatopropyltriethoxysilane, and the glycidoxypropyltrimethoxysilane:
   the 4-4'-diphenyl methane-isocyanate (MDI) is present in an amount of 76.5%,
   the castor oil is present in an amount of 20.6%,
   the isocyanatopropyltriethoxysilane is present in an amount of 1.0%, and
   the glycidoxypropyltrimethoxysilane is present in an amount of 1.9%.

9. The method of claim 1, wherein in the composition comprising the dicyclohexylmethane-4,4-diisocyanate, the polyether polyol, the 4,4'-diphenylmethane-diisocyanate (MDI), and the triethoxy (3-isocyanatopropyle) silane:
   the dicyclohexylmethane-4,4-diisocyanate is present in an amount of 20%,
   the polyether polyol is present in an amount of 55.24%,
   the 4,4'-diphenylmethane-diisocyanate (MDI) is present in an amount of 15.24%, and
   the triethoxy (3-isocyanatopropyle) silane is present in an amount of 9.52%.

10. The method of claim 1, wherein the second component comprises the polyoxypropylene oxide ether polyol, diol (2000 MW) in an amount of 53.5%, the polyxoypropylene oxide ether polyol, the triol (450 MW) in an amount of 25.8%, the tetrahydroxypropylethylendiamine in an amount of 17.9%, the metaxylenediamine in an amount of 2.6%, and the organobismuth catalyst in an amount of 0.2%.

11. A method, comprising:
   combining first and second components to produce a self-supporting curable polymer,
   wherein the first component is a reaction product of (a) composition comprising 76.5% 4-4'-diphenyl methane-isocyanate (MDI), 20.6% castor oil, 1.0% isocyanatopropyltriethoxysilane, and 1.9% glycidoxypropyltrimethoxysilane, and (b) a composition comprising 20% dicyclohexylmethane-4,4-diisocyanate, 55.24% polyether polyol, 15.24% 4,4'-diphenylmethane-diisocyanate (MDI), and 9.52% triethoxy (3-isocyanatopropyle) silane,
   wherein the second component comprises 53.5% polyoxypropylene oxide ether polyol, diol (2000 MW), 25.8% polyxoypropylene oxide ether polyol, 25.8% triol (450 MW), 17.9% tetrahydroxypropylethylendiamine, 2.6% metaxylenediamine, and 0.2% organobismuth catalyst; and
   allowing the polymer to cure for a period of time applying the polymer to a hoof or a claw of an ungulate animal.

12. A method, comprising:
   combining first and second components to produce a self-supporting curable polymer,
   wherein the first component is a reaction product of (a) a composition consisting of 4-4'-diphenyl methane-isocyanate (MDI), castor oil, isocyanatopropyltriethoxysilane, and glycidoxypropyltrimethoxysilane, and (b) a composition consisting of dicyclohexylmethane-4,4-diisocyanate, polyether polyol, 4,4'-diphenylmethane-diisocyanate (MDI), and triethoxy (3-isocyanatopropyle) silane;
   wherein the second component consists of polyoxypropylene oxide ether polyol, diol (2000 MW), polyxoypropylene oxide ether polyol, triol (450 MW), tetrahydroxypropylethylendiamine, metaxylenediamine, and organobismuth catalyst;
   wherein the curable polymer is self-supporting when applied onto a vertical surface; and allowing the polymer to cure for a period of time applying the polymer to a hoof or a claw of an ungulate animal.

* * * * *